US008471216B2

(12) United States Patent
Suda et al.

(10) Patent No.: US 8,471,216 B2
(45) Date of Patent: Jun. 25, 2013

(54) ELECTROSTATIC ATOMIZING DEVICE

(75) Inventors: Hiroshi Suda, Osaka (JP); Yukiyasu Asano, Hyogo (JP); Masaharu Machi, Kyoto (JP); Jumpei Oe, Shiga (JP); Yasuhiro Komura, Osaka (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 13/638,876

(22) PCT Filed: Apr. 15, 2011

(86) PCT No.: PCT/JP2011/059376
§ 371 (c)(1),
(2), (4) Date: Oct. 1, 2012

(87) PCT Pub. No.: WO2011/136044
PCT Pub. Date: Nov. 3, 2011

(65) Prior Publication Data

US 2013/0020497 A1 Jan. 24, 2013

(30) Foreign Application Priority Data

Apr. 30, 2010 (JP) ................................ 2010-105136

(51) Int. Cl.
*H01J 27/02* (2006.01)
*B05B 5/00* (2006.01)
*B05B 5/025* (2006.01)
*F23D 11/32* (2006.01)

(52) U.S. Cl.
USPC ....... 250/423 R; 250/425; 239/690; 239/706; 239/708; 313/359.1; 62/134

(58) Field of Classification Search
USPC .............. 250/423 R, 425; 239/690, 706, 708; 313/359.1; 62/134
See application file for complete search history.

(56) References Cited

U.S. PATENT DOCUMENTS

| | | | | |
|---|---|---|---|---|
| 8,191,805 | B2 * | 6/2012 | Nakada et al. | 239/690 |
| 8,282,028 | B2 * | 10/2012 | Nakada et al. | 239/690.1 |
| 8,360,341 | B2 * | 1/2013 | Machi et al. | 239/128 |

FOREIGN PATENT DOCUMENTS

| | | | |
|---|---|---|---|
| EP | 2050602 | A1 | 4/2009 |
| JP | 2003-294280 | A | 10/2003 |
| JP | 2005-164139 | A | 6/2005 |
| JP | 2006-068711 | A | 3/2006 |
| JP | 2009-193793 | A | 8/2009 |
| WO | WO-2007/111121 | A1 | 10/2007 |

OTHER PUBLICATIONS

International Search Report issued in International Application No. PCT/JP2011/059376 issued on May 24, 2011.

Extended European Search Report dated Jan. 17, 2013 issued in corresponding EP Patent Application No. 11774828.5.

* cited by examiner

*Primary Examiner* — Nikita Wells
(74) *Attorney, Agent, or Firm* — McDermott Will & Emery LLP

(57) ABSTRACT

An electrostatic atomizing device comprises an electrostatic atomizing part (2) applying high-voltage to water supplied to an atomization electrode (1), thereby generating negatively-charged minute water particles, a positive ion generator (3) being configured to generate positive ions, and a controller (16) being configured to control operation of said electrostatic atomizing part (2) and said positive ion generator (3). Said controller (16) controls so as to cause said electrostatic atomizing part (2) to generate the negatively-charged minute water particles, after the positive ions are generated by said positive ion generator (3).

5 Claims, 4 Drawing Sheets

ELECTROSTATIC ATOMIZING DEVICE

RELATED APPLICATIONS

This application is the U.S. National Phase under 35 U.S.C. §371 of International Application No. PCT/JP2011/059376, filed on Apr. 15, 2011, which in turn claims the benefit of Japanese Application No. 2010-105136, filed on Apr. 30, 2010, the disclosures of which Applications are incorporated by reference herein.

TECHNICAL FIELD

The invention relates to an electrostatic atomizing device.

BACKGROUND ART

An electrostatic atomizing device has been known, for instance, as disclosed in Japanese Patent Application Laid-Open No. 2006-68711, and is configured to apply high-voltage to the water that has been supplied to an atomization electrode, thereby generating negatively-charged minute water particles of nanometer sizes.

The charged minute water particles generated by the electrostatic atomizing device are emitted to a space. The emitted charged minute water particles are suspended within the space, and then come into contact with odor components, bacteria, allergenic materials and the like suspended within the space, thereby adhering to those. Or the emitted charged minute water particles come into contact with an inner wall in the space and substances existing in the space, thereby adhering to those.

As described above, the emitted charged minute water particles adheres to targets, and then radicals included in the emitted charged minute water particles deodorize and sterilize the targets, and inactivate the allergenic materials.

However, in the conventional electrostatic atomizing device, only a small percentage of the countless charged minute water particles emitted and suspended within the space incidentally comes into contact with the odor components, bacteria, and allergenic materials suspended within the space, or the inner wall in the space and the substances existing in the space, thereby adhering to those.

Further, the odor components, bacteria and allergenic materials, or the inner wall in the space and the substances existing in the space may be positively-charged or negatively-charged. In this case, the negatively-charged minute water particles are pulled and adheres, through action of the electrical attraction, with respect to the positively-charged odor components, bacteria, and allergenic materials. However, the negatively-charged minute water particles electrically repel the negatively-charged odor components, bacteria, and allergenic materials, and thereby can not adhere to those.

Accordingly, in the conventional electrostatic atomizing device, there is a problem that a very small percentage of the charged minute water particles emitted to the space adheres to the odor components, bacteria, and allergenic materials suspended within the space, or the inner wall in the space and the substances existing in the space.

DISCLOSURE OF THE INVENTION

It is an object of the present invention to provide an electrostatic atomizing device, which can cause charged minute water particles to effectively adhere to odor components, bacteria and allergenic materials suspended within a space to which the charged minute water particles are emitted, or an inner wall in the space and substances existing in the space.

An electrostatic atomizing device of the present invention comprises: an electrostatic atomizing part applying high-voltage to water supplied to an atomization electrode, thereby generating negatively-charged minute water particles; a positive ion generator being configured to generate positive ions; and a controller being configured to control operation of said electrostatic atomizing part and said positive ion generator, and wherein said controller controls so as to cause said electrostatic atomizing part to generate the negatively-charged minute water particles, after the positive ions are generated by said positive ion generator.

In this configuration, since said controller controls so as to cause said electrostatic atomizing part to generate the negatively-charged minute water particles after the positive ions are generated by said positive ion generator, the electrostatic atomizing device can cause the negatively-charged minute water particles to effectively adhere to targets being positively-charged previously.

Further, preferably, the electrostatic atomizing device comprises a high-voltage power source supplying high-voltage to said electrostatic atomizing part and said positive ion generator, and wherein said electrostatic atomizing part comprises said atomization electrode to which water is supplied, and an opposed atomization electrode which is disposed in an opposed relation to said atomization electrode, and wherein said positive ion generator comprises an electric discharging electrode, and an opposed electric discharging electrode which is disposed in an opposed relation to said electric discharging electrode, and wherein said atomization electrode and said opposed electric discharging electrode are connected to a low electric potential side of said high-voltage power source, and wherein said opposed atomization electrode and said electric discharging electrode are connected to a high electric potential side of said high-voltage power source.

Further, preferably, the electrostatic atomizing device comprises a first switch for switching on and off the generation of the negatively-charged minute water particles in said electrostatic atomizing part, and a second switch for switching on and off the generation of the positive ions in said positive ion generator.

Further, preferably, the electrostatic atomizing device comprises a detection sensor for detecting a substance being a target for inactivation, such as dust, allergen or odor, existing in a space to which the negatively-charged minute water particles are emitted, and wherein said controller controls so as to cause said positive ion generator to change the amount of generation of the positive ions and so as to cause said electrostatic atomizing part to change the amount of generation of the negatively-charged minute water particles, in response to the degree of dirt in said space detected by said detection sensor.

Further, preferably, the electrostatic atomizing device comprises a human body detection sensor for detecting a human body, and wherein when said human body detection sensor does not detect a human body, said controller controls so as to cause said electrostatic atomizing part to generate the negatively-charged minute water particles after the positive ions are generated by said positive ion generator, and wherein when said human body detection sensor detects a human body, said controller controls so as to switch off the generation of the positive ions in said positive ion generator and so as to cause said electrostatic atomizing part to generate the negatively-charged minute water particles.

BRIEF DESCRIPTION OF THE DRAWINGS

Preferred embodiments of the invention will now be described in further details. Other features and advantages of the present invention will become better understood with regard to the following detailed description and accompanying drawings where.

BEST MODE FOR CARRYING OUT THE INVENTION

Embodiments of the present invention will be explained below referring to Figures.

Figure 1:
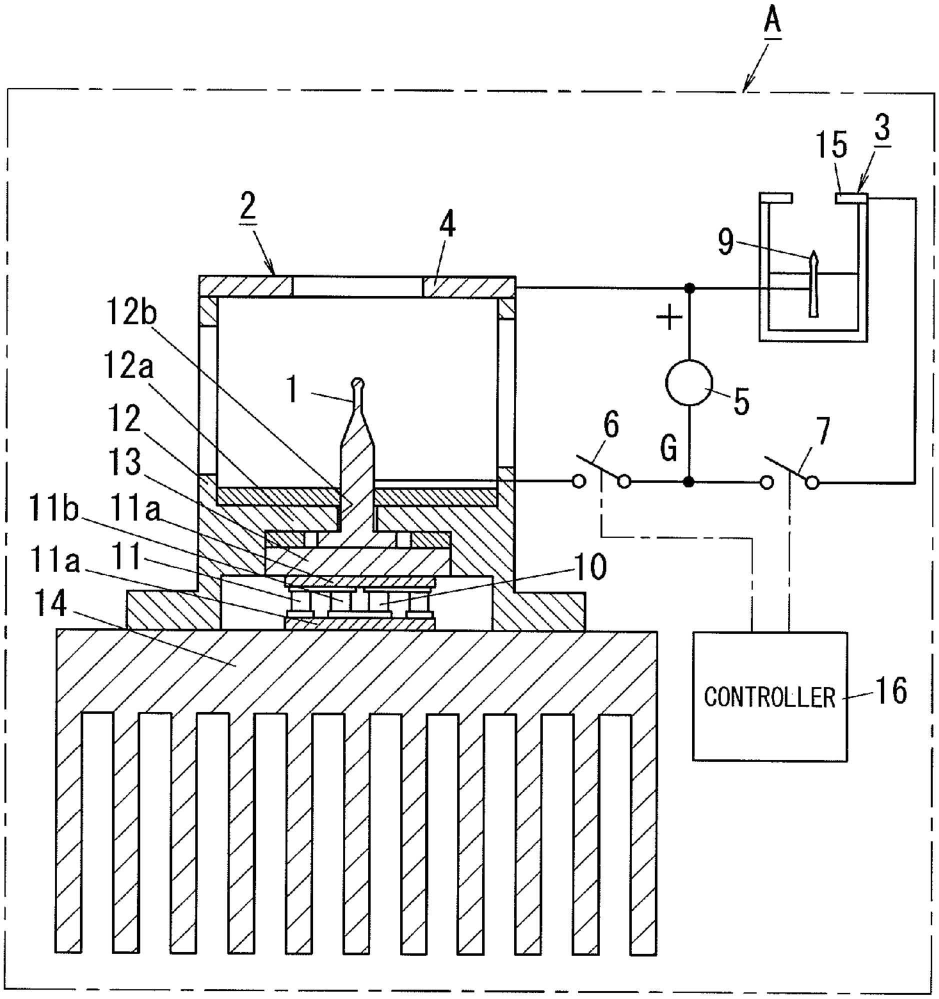
FIG. 1 is a schematic configuration diagram of an electrostatic atomizing device according to an Embodiment of the present invention.

FIG. 1 show a schematic configuration diagram of an electrostatic atomizing device A. The electrostatic atomizing device A comprises: an electrostatic atomizing part 2 that is configured to generate negatively-charged minute water particles; a positive ion generator 3 that is configured to generate positive ions; a high-voltage power source 5; and a controller 16.

The electrostatic atomizing part 2 comprises an atomization electrode 1, an opposed atomization electrode 4 disposed in an opposed relation to the atomization electrode 1, and a water supply means 10 for supplying water to a tip of the atomization electrode 1. Then, the high-voltage power source 5 applies high-voltage to water supplied to the tip of the atomization electrode 1.

As shown in FIG. 1, the water supply means 10 comprises a cooling means, such as a Peltier unit 11. That is, the water supply means 10 causes the Peltier unit 11, being the cooling means, to cool water included in the air and supplies dew condensation water to the tip of the atomization electrode 1. In addition, the water supply means 10 is not limited to this configuration, and may be configured to cause a water tank (not shown in the figure) to supply, through capillary action or pressurization, water held in the tank to the tip of the atomization electrode 1. Or the water supply means 10 may be configured to supply water to the tip, through flowing water downward or dropping water using a force of gravitation.

Further, as shown in FIG. 1, the electrostatic atomizing device A comprises a main casing 12 that has insulation property and is formed into a tubular shape. Then, the inside of the main casing 12 is divided into two regions by a partition 12*a*. The Peltier unit 11, being the water supply means 10, is disposed in one (a lower half in FIG. 1) of the two regions into which the inside of the main casing 12 is divided by the partition 12*a*. The other (an upper half in FIG. 1) of the two regions is an electrostatic atomizing chamber.

The Peltier unit 11, as shown in FIG. 1, comprises a pair of Peltier circuit boards 11*a*, 11*a* which are disposed in an opposed relation to each other, and a plurality of thermoelectric elements 11*b* which are installed in a row. The plurality of thermoelectric elements 11*b* are held between Peltier circuit boards 11*a*, 11*a*, and the adjacent thermoelectric elements 11*b* are electrically connected to each other through both circuit boards. The Peltier unit 11 is configured so that when current flows in thermoelectric elements 11*b* through a Peltier input lead wire (not shown), heat moves from one Peltier circuit board 11*a* to the other Peltier circuit board 11*a*.

Further, as shown in FIG. 1, the electrostatic atomizing device A comprises a cooling unit 13 and a heat release unit 14. The cooling unit 13 is connected to the outer side of a Peltier circuit board 11*a* located in one side (an upper side in FIG. 1). Then, the heat release unit 14 is connected to the outer side of a Peltier circuit board 11*a* located in the other side (a lower side in FIG. 1). In the present embodiment, a radiation fin is used as the heat release unit 14.

The atomization electrode 1 penetrates through a hole 12*b* provided in the partition 12*a* of the main casing 12 and projects into the electrostatic atomizing chamber, while a rear end portion of the atomization electrode 1 is connected to the cooling unit 13 side of the Peltier unit 11.

The opposed atomization electrode 4 is formed into a ring shape and is provided in an opening portion formed in the tip of the tubular-shaped main casing 12.

Then, as shown in FIG. 1, the atomization electrode 1 is connected to a low electric potential side of the high-voltage power source 5, and the opposed atomization electrode 4 is connected to a high electric potential side of the high-voltage power source 5. The low electric potential side of the high-voltage power source 5 is grounded.

The electrostatic atomizing part 2 having the abovementioned configuration is provided with a first switch 6. When the first switch 6 is switched on, high-voltage is applied between the atomization electrode 1 and the opposed atomization electrode 4. Then, electrostatic atomizing part 2 is configured to generate negatively-charged minute water particles by electrostatically atomizing water supplied to the tip of the atomization electrode 1.

Specifically, the current flows in the Peltier unit 11 and then the cooling unit 13 is cooled, and thereby the atomization electrode 1 is also cooled and then water that is included in the air within the main casing 12 is concentrated at the tip of the atomization electrode 1. That is, water (dew condensation water) is supplied to the tip of the atomization electrode 1. Then, when the first switch 6 is switched on, the high-voltage power source 5 applies high-voltage to the dew condensation water supplied to the tip of the atomization electrode 1. Then, the surface of the dew condensation water locally rises so as to be formed into a cone shape. Therefore, a Taylor cone is formed. Then, the electrical charge is concentrated at a tip of the Taylor cone, and thereby the electrical field intensity at the tip becomes large and further develops the Taylor cone. When the charge density is increased by the development of the Taylor cone and the concentration of the electrical charge at the tip of the Taylor cone, the tip of the Taylor cone receives a large amount of energy (a repulsion force due to the high charge density). In this way, when the tip of the Taylor cone receives a large amount of energy, the energy becomes larger than the surface tension of the water and then the breakups and the spread (Rayleigh breakup) of the Taylor cone are repeated, and thereby the negatively-charged minute water particles of nanometer sizes are generated in large numbers. The charged minute water particles include radicals (active species), such as OH radicals (hydroxyl radicals).

As shown in FIG. 1, the positive ion generator 3 comprises an electric discharging electrode 9, and an opposed electric discharging electrode 15 which is disposed in an opposed relation to the electric discharging electrode 9. Then, the high-voltage power source 5 applies high-voltage not only to the electrostatic atomizing part 2 but also to the positive ion generator 3. That is, the positive ion generator 3 and the electrostatic atomizing part 2 share one high-voltage power source 5. Therefore, the entire electrostatic atomizing device A can be downsized. Needless to say, instead of the high-voltage power source 5, two high-voltage power sources (not shown) may be located within the electrostatic atomizing part 2 and the positive ion generator 3, respectively, and thus the part 2 and the generator 3 may be configured to receive the power supply separately.

Then, as shown in FIG. 1, the electric discharging electrode 9 of the positive ion generator 3 is connected to a high electric potential side of the high-voltage power source 5, and the opposed electric discharging electrode 15 is connected to a low electric potential side of the high-voltage power source 5.

The positive ion generator 3 having the above configuration is provided with a second switch 7. When the second switch 7 is switched on, high-voltage is applied between the electric discharging electrode 9 and the opposed electric discharging electrode 15, and thereby atmospheric discharge is performed and then the positive ions are generated.

The controller 16 is configured to control operation of electrostatic atomizing part 2 and positive ion generator 3 by controlling on/off operation of the first and second switches 6, 7.

Here, the controller 16 of the present embodiment activates only the positive ion generator 3, by switching on the second switch 7, in a state where the first switch 6 is being switched off. That is, the electrostatic atomizing device A of the present embodiment generates and emits only positive ions to a space first.

Then, the controller 16 switches off the second switch 7 after a predetermined period has elapsed, thereby deactivating the positive ion generator 3. Then, the controller 16 switches on the first switch 6 in synchronization with the off-operation of the second switch 7 or after a certain period from the off-operation of the second switch 7, thereby activating the electrostatic atomizing part 2. That is, the electrostatic atomizing device A of the present embodiment generates and emits the negatively-charged minute water particles of nanometer sizes to the space after emitting the positive ions to the space. In this case, the first switch 6 may be switched off automatically by the controller 16, after a predetermined period has elapsed from the on-operation of the first switch 6. Alternatively, the first switch 6 may be switched off by hand of a user.

In addition, the controller 16 may control so as to activate alternately the positive ion generator 3 and the electrostatic atomizing part 2, thereby generating alternately the positive ions and the negatively-charged minute water particles to emit to the space.

As explained above, the electrostatic atomizing device A of the present embodiment controls so as to drive the positive ion generator 3, before drive of the electrostatic atomizing part 2, and thereby can improve the adherence efficiency of the negatively-charged minute water particles of nanometer sizes, including radicals, generated through the drive of the electrostatic atomizing part 2, as explained below.

The action of the electrostatic atomizing device A of the present embodiment will be explained below more specifically.

First, the controller 16 controls so as to switch on the second switch 7, thereby activating the positive ion generator 3 and generating the positive ions. Therefore, the positive ions are emitted to a space and are suspended within the space.

Then, the countless positive ions suspended within the space adhere to odor components, bacteria, allergenic materials and the like suspended within the space. Or the countless positive ions adhere to an inner wall (a wall surface, a ceiling surface, a floor surface or the like) in the space and substances existing in the space. Then, through the adherence of the positive ions, the abovementioned materials, substances and inner wall become positively-charged.

In this case, the abovementioned materials, substances and inner wall may already be positively-charged or negatively-charged, even before the adherence of the emitted positive ions.

However, when the abovementioned materials, substances and inner wall already are positively-charged, the emitted positive ions repel those, thereby not adhering to those. Therefore, those are kept in the positively-charged status.

Then, when the abovementioned materials, substances and inner wall already are negatively-charged, the emitted positive ions are pulled by those. Therefore, negative electrostatic charges in those change smaller, change to the electrically neutral status, or change to the positively-charged status.

Therefore, even if odor components, bacteria and allergenic materials suspended within the space, or inner wall in the space and substances existing in the space already are positively-charged or negatively-charged before the adherence of the positive ions, the electrostatic atomizing device A of the present embodiment emits the positive ions to the space and thereby can make a positively-charged environment in the space, or an environment where the negatively-charged minute water particles do not repel the odor components, bacteria and allergenic materials, or the inner wall in the space and the substances existing in the space.

When a predetermined period has elapsed from start of operation of the positive ion generator 3 in the abovementioned way, the controller 16 controls to switch off the second switch 7, thereby stopping the operation of the positive ion generator 3. Then, the controller 16 controls to switch on the first switch 6 in synchronization with the off-operation of the second switch 7 or after a certain period from the off-operation of the second switch 7, thereby starting operation of the electrostatic atomizing part 2. That is, the electrostatic atomizing part 2 generates the negatively-charged minute water particles to emit to the space.

Then, the negatively-charged minute water particles are suspended within the space under the positively-charged environment.

The countless negatively-charged minute water particles suspended within the space adhere to the positively-charged odor components, bacteria, allergenic materials and the like suspended within the space, through action of the electrical attraction. Or the countless negatively-charged minute water particles adhere to the positively-charged inner wall and substances existing in the space, through action of the electrical attraction. In this way, through action of the electrical attraction, the negatively-charged minute water particles of nanometer sizes, including radicals, can adhere to the odor components, bacteria, allergenic materials and the like suspended within the space, or the inner wall and substances existing in the space.

In addition, some of the negatively-charged minute water particles suspended within the space are pulled by the positive ions suspended within the space, thereby changing to neutral minute water particles, including radicals. Then, the neutral minute water particles, including radicals, are continuously suspended with in the space, and adheres to the odor components, bacteria, allergenic materials and the like suspended within the space, or the inner wall and substances existing in the space.

As described above, some of the countless negatively-charged minute water particles emitted to the space are electrically neutralized and then adheres while being suspended within the space, but many of the countless negatively-charged minute water particles adhere without being electrically neutralized, through action of the electrical attraction. As a result, the adherence efficiency at large can be improved.

Therefore, the electrostatic atomizing device A of the present embodiment can cause the negatively-charged minute water particles of nanometer sizes, including radicals, generated by the electrostatic atomizing part 2, to effectively adhere to the odor components, bacteria and allergenic materials suspended within the space, or the inner wall and substances existing in the space. Therefore, the inactivating effect of the allergenic materials, the deodorizing effect and the sterilizing effect can be improved.

Next, another embodiment of the present invention will be explained below referring to FIG. 2.

Figure 2:
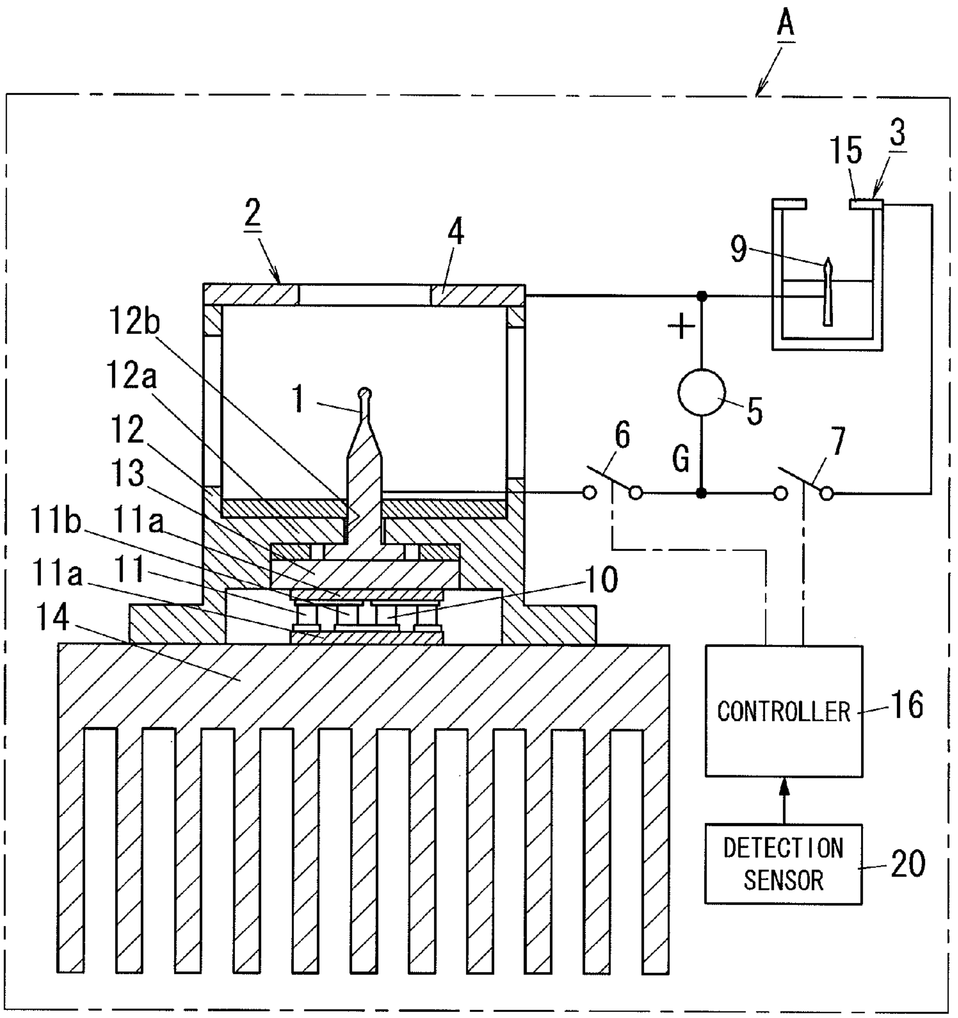
FIG. 2 is a schematic configuration diagram of an electrostatic atomizing device according to another Embodiment of the present invention.

An electrostatic atomizing device A shown in FIG. 2 is characterized by further comprising a detection sensor 20 (for example, a dust sensor, an allergen sensor, an odor sensor or the like) for detecting a substance being a target for inactivation, such as dust, allergen or odor, existing in the space to which the negatively-charged minute water particles are emitted. The other configuration is similar to the configuration of the embodiment shown in FIG. 1, and explanation thereof is herein omitted.

The detection sensor 20 is configured to output, to the controller 16, the information (for example, concentration data of dust, allergen or the like within the space) regarding the detected dirt within the space. Then, the controller 16 controls so as to change the amount of generation of the positive ions and the amount of generation of the negatively-charged minute water particles, in response to the degree of dirt in the space.

Specifically, a table expressing, for example, multiple concentration data and the amount data of generation of the positive ions and the negatively-charged minute water particles corresponding to the respective multiple concentration data is stored previously in a memory (not shown in the figure). When obtaining concentration data regarding dirt from the detection sensor 20, the controller 16 determines, from the table, the amount data of generation the positive ions and the negatively-charged minute water particles corresponding to the concentration data. Then, the controller 16 controls the positive ion generator 3 and the electrostatic atomizing part 2, based on the amount data of generation determined from the table.

In this case, the amount data of generation in the abovementioned table are set so that the amount of generation of the positive ions and the negatively-charged minute water particles increases more with the increase in concentration data. That is, when the degree of dirt within the space is high, the controller 16 controls so as to cause the positive ion generator 3 to increase the amount of generation of the positive ions, and so as to cause the electrostatic atomizing part 2 to increase the amount of generation of the negatively-charged minute water particles. In contrast, when the degree of dirt within the space is low, the controller 16 controls so as to cause the positive ion generator 3 to reduce the amount of generation of the positive ions, and so as to cause the electrostatic atomizing part 2 to reduce the amount of generation of the negatively-charged minute water particles.

In regard to the increase or decrease in the amount of generation of the positive ions and the negatively-charged minute water particles, the conventional publicly known method may be used. As one example of such a method, the increase or decrease in the amount of generation can be realized by means of adjusting the respective times to apply high-voltage to the positive ion generator 3 and the electrostatic atomizing part 2.

In this way, the electrostatic atomizing device A shown in FIG. 2 can effectively inactivate a substance being a target for inactivation, such as dust, allergen or odor, in response to the degree of dirt in the space, through radicals included in the negatively-charged minute water particles.

Then, yet another embodiment of the present invention will be explained below referring to FIG. 3 and FIG. 4.

Figure 3:
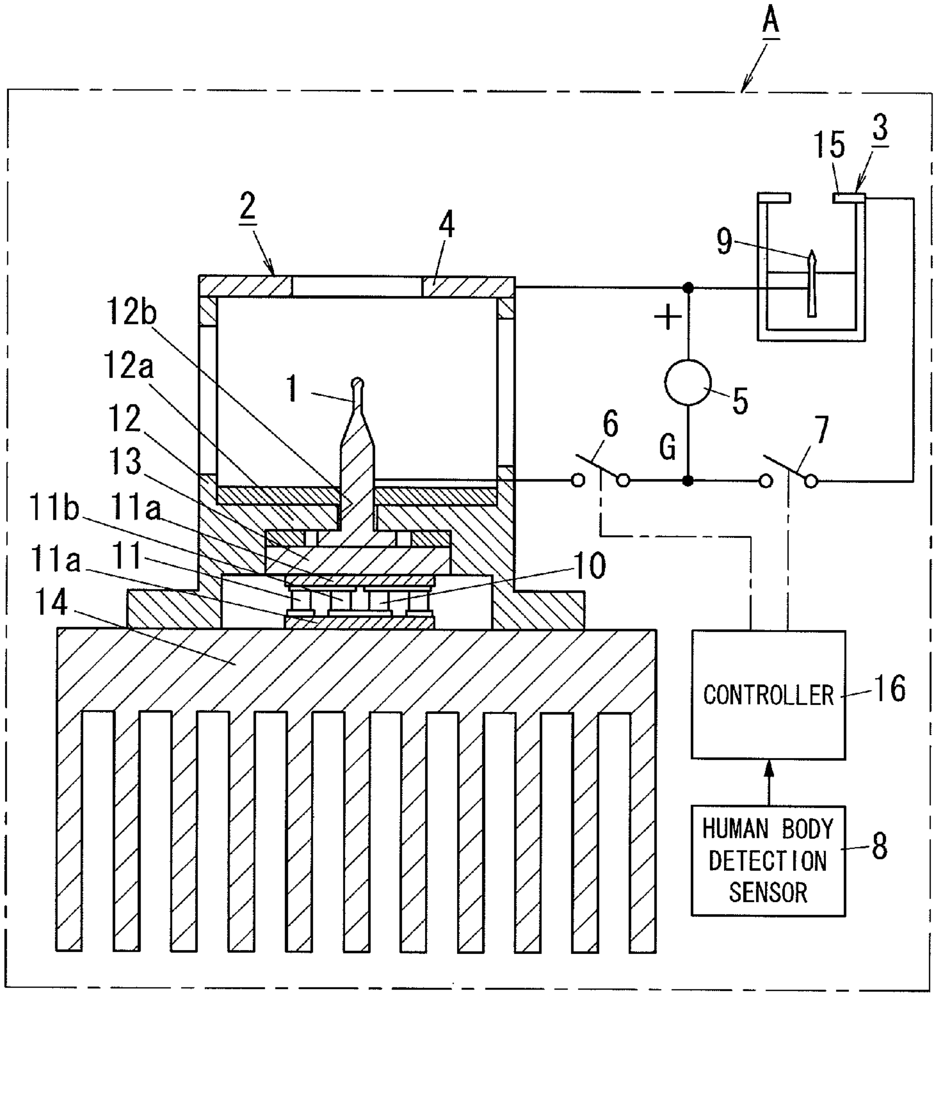
FIG. 3 is a schematic configuration diagram of an electrostatic atomizing device according to yet another Embodiment of the present invention.

An electrostatic atomizing device A shown in FIG. 3 is characterized by further comprising a human body detection sensor 8 for detecting a human body in the space. The other configuration is similar to the configuration of the embodiment shown in FIG. 1, and explanation thereof is herein omitted. The human body detection sensor 8 is configured to output the information regarding the presence of absence of a human body to the controller 16.

When the human body detection sensor 8 does not detect a human body, as well as the abovementioned embodiments, the controller 16 controls so as to cause the electrostatic atomizing part 2 to generate the negatively-charged minute water particles after the positive ions are generated by the positive ion generator 3.

Meanwhile, when the human body detection sensor 8 detects a human body, the controller 16 controls to switch off the positive ion generator 3 and to activate the electrostatic atomizing part 2 and to cause the electrostatic atomizing part 2 to generate the negatively-charged minute water particles to emit to the space.

Typically, it is said that when a person is in the space and the positive ions are emitted to the space, the emission of the positive ions gives the person stress. However, as explained above, the electrostatic atomizing device A shown in FIG. 3 generates and emits only the negatively-charged minute water particles to the space without emitting the positive ions, when a person is in the space. As a result, the electrostatic atomizing device A can realize the inactivation of the allergenic materials, the deodorization and the sterilization in the space without giving the person stress.

Figure 4:
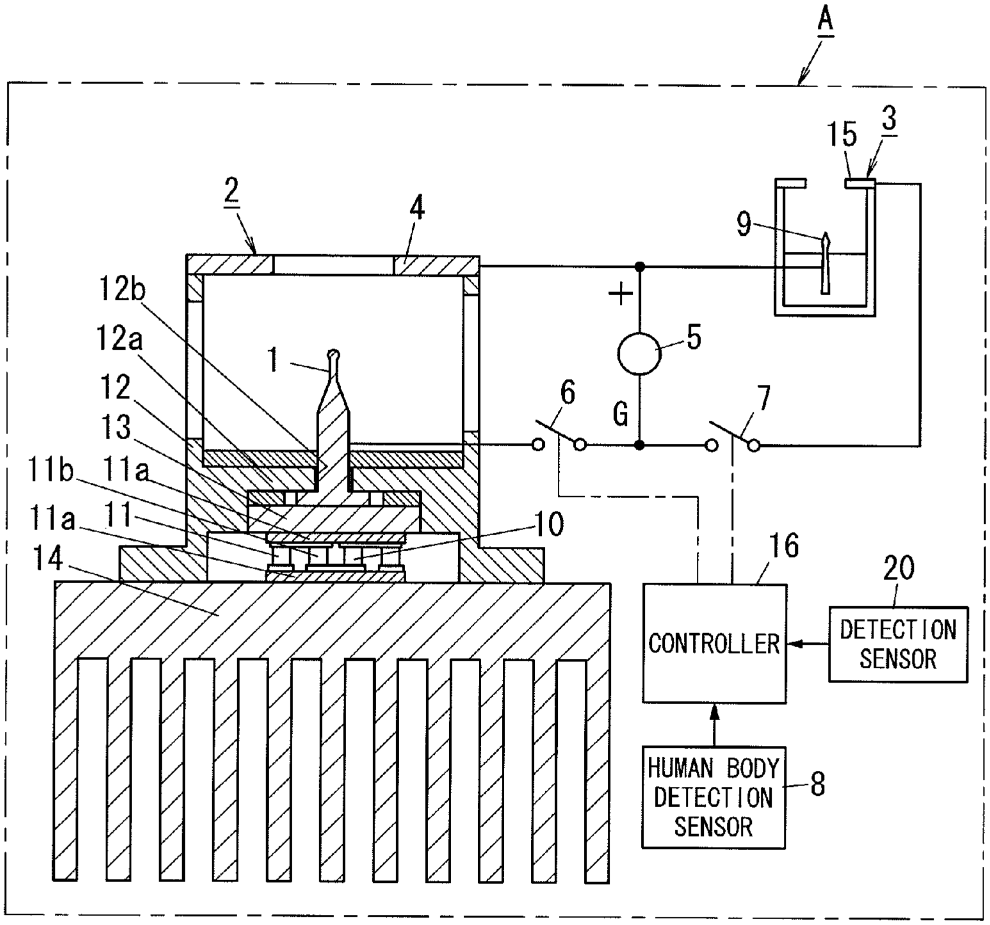
FIG. 4 is a schematic configuration diagram of an electrostatic atomizing device according to yet another Embodiment of the present invention.

In addition, an electrostatic atomizing device A shown in FIG. 4 comprises both of the abovementioned detection sensor 20 and human body detection sensor 8. Therefore, the electrostatic atomizing device A can effectively can realize the inactivation of the allergenic materials, the deodorization and the sterilization, in response to the degree of dirt, without giving a person stress.

Although the present invention has been described with reference to certain preferred embodiments, numerous modifications and variations can be made by those skilled in the art without departing from the true spirit and scope of this invention, namely claims.

The invention claimed is:

1. An electrostatic atomizing device comprising:

an electrostatic atomizing part applying high-voltage to water supplied to an atomization electrode, thereby generating negatively-charged minute water particles;

a positive ion generator being configured to generate positive ions; and a controller being configured to control operation of said electrostatic atomizing part and said positive ion generator, wherein said controller controls so as to cause said electrostatic atomizing part to generate the negatively-charged minute water particles, after the positive ions are generated by said positive ion generator.

2. The electrostatic atomizing device as claimed in claim 1, further comprising a high-voltage power source supplying high-voltage to said electrostatic atomizing part and said positive ion generator, wherein said electrostatic atomizing part comprises said atomization electrode to which water is supplied, and an opposed atomization electrode which is disposed in an opposed relation to said atomization electrode, wherein said positive ion generator comprises an electric discharging electrode, and an opposed electric discharging electrode which is disposed in an opposed relation to said electric discharging electrode, wherein said atomization electrode and said opposed electric discha- rging electrode are connected to a low electric potential side of said high- voltage power source, wherein said opposed atomization electrode and said electric discha- rging electrode are connected to a high electric potential side of said high- voltage power source.

3. The electrostatic atomizing device as claimed in claim 2, further comprising a first switch for switching on and off the generation of the negatively-charged minute water particles in said electrostatic atomizing part, and a second switch for switching on and off the generation of the positive ions in said positive ion generator.

4. The electrostatic atomizing device as claimed in claim 1, further comprising a detection sensor for detecting a substance being a target for inactivation, such as dust, allergen or odor, existing in a space to which the negatively-charged minute water particles are emitted, wherein said controller controls so as to cause said positive ion generator to change the amount of generation of the positive ions and so as to cause said electrostatic atomizing part to change the amount of generation of the negatively-charged minute water particles, in response to the degree of dirt in said space detected by said detection sensor.

5. The electrostatic atomizing device as claimed in claim 1, further comprising a human body detection sensor for detecting a human body, wherein when said human body detection sensor does not detect a human body, said controller controls so as to cause said electrostatic atomizing part to generate the negatively-charged minute water particles after the positive ions are generated by said positive ion generator, wherein when said human body detection sensor detects a human body, said controller controls so as to switch off the generation of the positive ions in said positive ion generator and so as to cause said electrostatic atomizing part to generate the negatively-charged minute water particles.

* * * * *